United States Patent [19]

Haught

[11] Patent Number: 4,546,774
[45] Date of Patent: Oct. 15, 1985

[54] LEVELING DEVICE FOR HEMODYNAMIC MONITORING TRANSDUCER ASSEMBLY

[76] Inventor: Robert M. Haught, 1800 NW. 4th Ave., Apt. #15A, Boca Raton, Fla. 33432

[21] Appl. No.: 469,465

[22] Filed: Feb. 24, 1983

[51] Int. Cl.⁴ ............................................. A61B 5/02
[52] U.S. Cl. ..................................... 128/673; 33/392
[58] Field of Search ............................. 128/672–673, 128/675, 748; 33/369, 379, 389, 392

[56] References Cited

U.S. PATENT DOCUMENTS

| | | | |
|---|---|---|---|
| 1,176,439 | 3/1916 | Falls | 33/369 |
| 3,996,927 | 12/1976 | Frank | 128/673 |
| 4,335,522 | 6/1982 | Canfield | 33/392 X |
| 4,419,833 | 12/1983 | Wright | 33/389 X |
| 4,431,009 | 2/1984 | Marino, Jr. et al. | 128/675 X |

*Primary Examiner*—Lee S. Cohen
*Assistant Examiner*—Angela D. Sykes
*Attorney, Agent, or Firm*—Oltman and Flynn

[57] ABSTRACT

For use in adjusting a hemodynamic transducer assembly on an IV stand to the level of the right atrium of a patient's heart, an elongated flexible line carries a small bubble level and has a loop at one end for insertion on the transducer assembly and a spring clip on the opposite end for attachment to an adhesive patch on the side of the patient's chest at the level of the right atrium.

6 Claims, 3 Drawing Figures

LEVELING DEVICE FOR HEMODYNAMIC MONITORING TRANSDUCER ASSEMBLY

BACKGROUND OF THE INVENTION

Hemodynamic monitoring of hospital patients requires that the zero (air) port of the monitoring transducer assembly be at the same level as the right atrium of the patient's heart.

For example, a SWAN-GANZ ® catheter is used to monitor pulmonary artery pressures in patients suffering from massive shock or trauma, various heart conditions, cirrhosis of the liver, or pertonitis, and patients undergoing extensive surgery. Such catheters have a major lumen for measuring pulmonary artery pressures and a small lumen for inflating and deflating the catheter balloon with air or $CO_2$. In addition, there may be a third lumen which receives a thermistor wire for determining blood temperature and a fourth lumen to monitor the right atrial (central venous) pressure.

The patient normally lies horizontal, as shown in FIG. 1, or in a semi-Fowler's position. Next to the patient's bed is an IV stand having a tubular vertical post 10 on which is adjustably mounted a unitary assembly which includes a strain gauge transducer 11 and a sterile transducer dome 12 directly above it. In the apparatus shown in FIG. 1, two transducer arms 13 and 14 extend up from the dome, one (13) inclined toward the patient and the other (14) vertical. Stopcocks 15 and 16 are located on the transducer arms and an "intraflow" 17 is connected between the stopcock 15 on the transducer arm 13 pointing toward the patient and a flexible tube 18 leading to the patient. The transducer assembly is slidably adjustable along the post 10 of the IV stand, and it has a manually operable clamping arrangement (not shown) for clamping it to the post at whatever height to which it is adjusted.

Stopcock 15 has an upwardly inclined, hollow, arm of cylindrical cross-section which is closed by a removable end cap 15a. When this cap is removed the transducer dome 12 is vented to the atmosphere through this hollow arm of stopcock 15. The other stopcock 16 has a similar hollow arm which, as shown in FIG. 1, extends horizontally and is closed by a removable end cap 16a. When end cap 16a is removed, the transducer dome 12 is vented to the atmosphere through this hollow arm of stopcock 16. Therefore, either stopcock 15 or 16 may be used to provide the zero port for calibrating the transducer 11. This zero port should be at the level of the right atrium, called the "reference level", which is the fourth sternal intracostal space, mid axially. As stated in "Monitoring Pulmonary Artery Pressures" by Susan L. Woods in The American Journal of Nursing, November 1976, Vol. 76, No. 11, the preferred reference level, suitable for persons of any build and in various positions, is a horizontal line drawn through the phelbostatic axis, which is the junction between a transverse plane at the fourth sternal intercostal space and a frontal plane midway between the anterior and posterior chest surfaces.

Prior to the present invention, the usual practice has been for the nurse to locate and mark the reference level on the patient's chest, after which an elongated carpenter's level is held horizontally between this mark on the patient's chest and the IV stand. The unitary assembly of the transducer, dome, transducer arms, stopcocks and intraflow is adjusted vertically along this stand until it is the same height as the reference level, as shown by the carpenter's level extending between it and the patient. This is inconvenient for the nurse and it can be upsetting to the patient, who often is at least partly conscious.

SUMMARY OF THE INVENTION

The present invention is directed to a novel arrangement for achieving the same result but with much less inconvenience to both the nurse and the patient.

In accordance with the presently preferred embodiment of this invention, a small bubble level is on a flexible line, one end of which is releasably attachable to the side of the patient's chest at the reference level and the opposite end of which carries an "eye" loop for insertion over a stopcock which provides the zero port for the transducer assembly on the IV stand. With one end of the line at the reference level on the side of the patient's chest, the nurse can concentrate on adjusting the transducer assembly vertically on the IV stand to a position in which the bubble level shows that the line is horizontal, which means that the transducer assembly is correctly positioned at the level of the right atrium of the patient's heart.

A principal object of this invention is to provide a novel leveling device for use with a hemodynamic monitoring transducer assembly to facilitate adjusting it to the same height as the right atrium of the patient's heart.

Another object of this invention is to provide such a leveling device which is more convenient for hospital personnel to use and is less likely to upset or disturb the patient than previously used arrangements for the same purpose.

Another object of this invention is to provide such a leveling device which may be used with vertically adjustable hemodynamic monitoring transducer assemblies of various designs.

Further objects and advantages of this invention will be apparent from the following detailed description of two presently preferred embodiments which are illustrated schematically in the accompanying drawing.

Before explaining the disclosed embodiment of the present invention in detail, it is to be understood that the invention is not limited in its application to the details of the particular arrangements shown since the invention is capable of other embodiments. Also, the terminology used herein is for the purpose of description and not of limitation.

DETAILED DESCRIPTION

Figure 1:
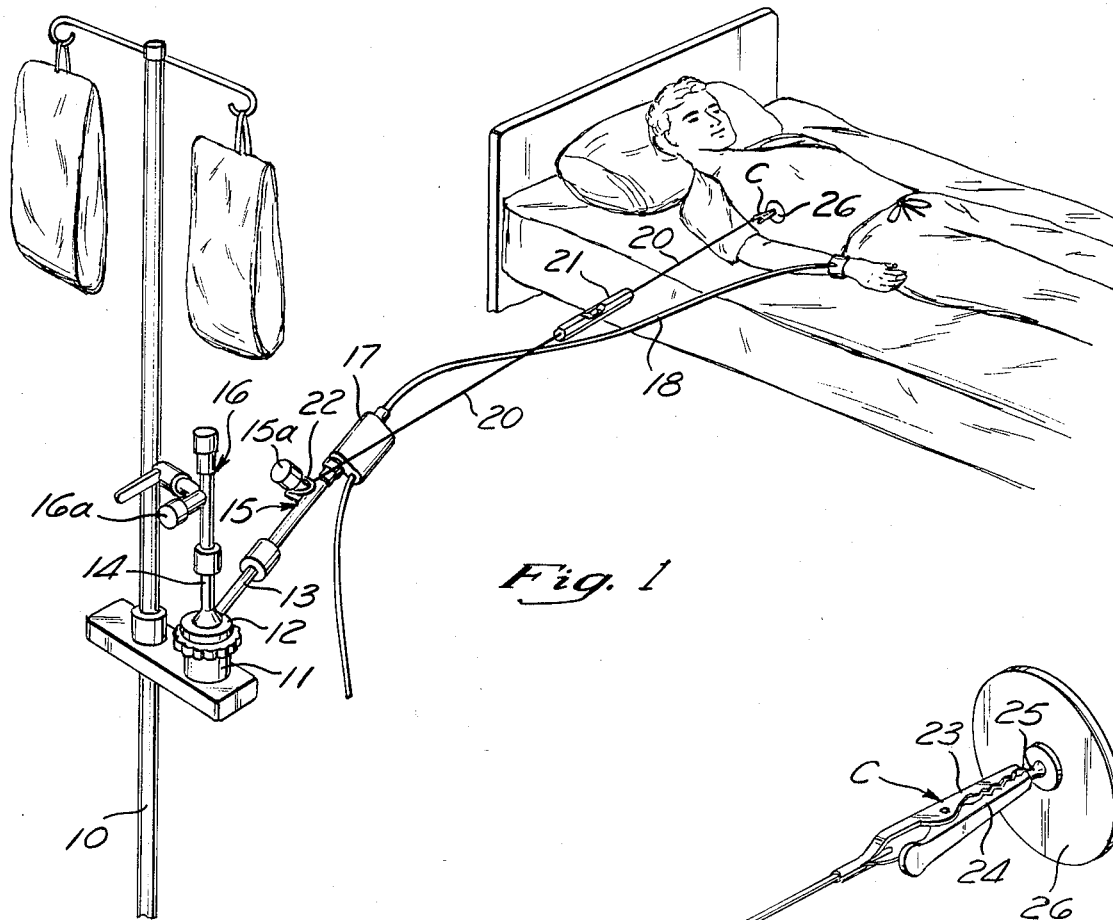
FIG. 1 is a perspective view showing the leveling device of the present invention applied to a patient and a hemodynamic monitoring transducer assembly on an IV stand.

In the embodiment shown in FIG. 1, the present leveling device comprises an elongated, small diameter, flexible line 20 of suitable textile material carrying a small bubble level 21 of known design intermediate its ends. On one end the line carries an "eye" loop 22 of suitable plastic or metal, and on its opposite end the line is attached to a so-called "alligator" clip C, having hinged, opposed, serrated jaws 23 and 24 which are biased toward each other by a spring (not shown).

The jaws of the clip C are engageable with and detachable from a metal post 25 extending from an adhesive patch 26 which the nurse applies to the side of the patient's chest (FIG. 1) at the reference level, as already explained. This adhesive patch 26 and post 25 may, if desired, be a heart monitoring electrode of known design.

The eye loop 22 is insertable over the hollow arm of the stopcock 15 which, as already explained, has an end cap 15a which may be removed to vent the transducer 11 to the atmosphere and thus provide the zero port for calibrating the equipment.

Alternatively, the eye loop 22 may be inserted over the corresponding arm of the other stopcock 16 in the transducer assembly, which has an end cap 16a that is removable to provide the zero port for the equipment.

In one practical embodiment, the line 20 is about six inches long between the eye loop 22 and the bubble level 21, the bubble level itself is two inches long and very light in weight, and the line 20 is twenty inches long from the bubble level 21 to the clip. This puts the bubble level 21 at a convenient location for observation by the nurse as she adjusts the transducer assembly vertically along the IV post 10 until the bubble shows that the zero port in the transducer assembly is at substantially the same height as the reference level of the patient's heart, as determined by the attachment of the clip C to the post 25. The line 20 is kept substantially taut by positioning the post 10 of the IV stand the proper distance from the patient, as shown in FIG. 1. This can be done without bothering the patient once the clip C is in place at the patient's chest, and all that remains is for the nurse to adjust the transducer assembly vertically along the IV stand.

Figure 3:
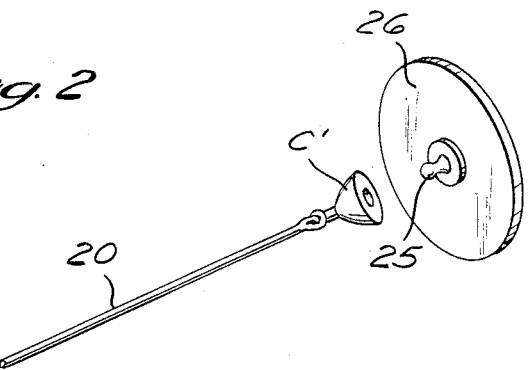
FIG. 3 is a fragmentary perspective view showing a different type of spring clip on the patient's end of the present leveling device.

FIG. 3 shows a modification in which the "alligator" clip C is replaced by a snap clip C' of known design which is insertable on the rounded, enlarged outer end of the post 25 on the adhesive patch 26.

Figure 2:
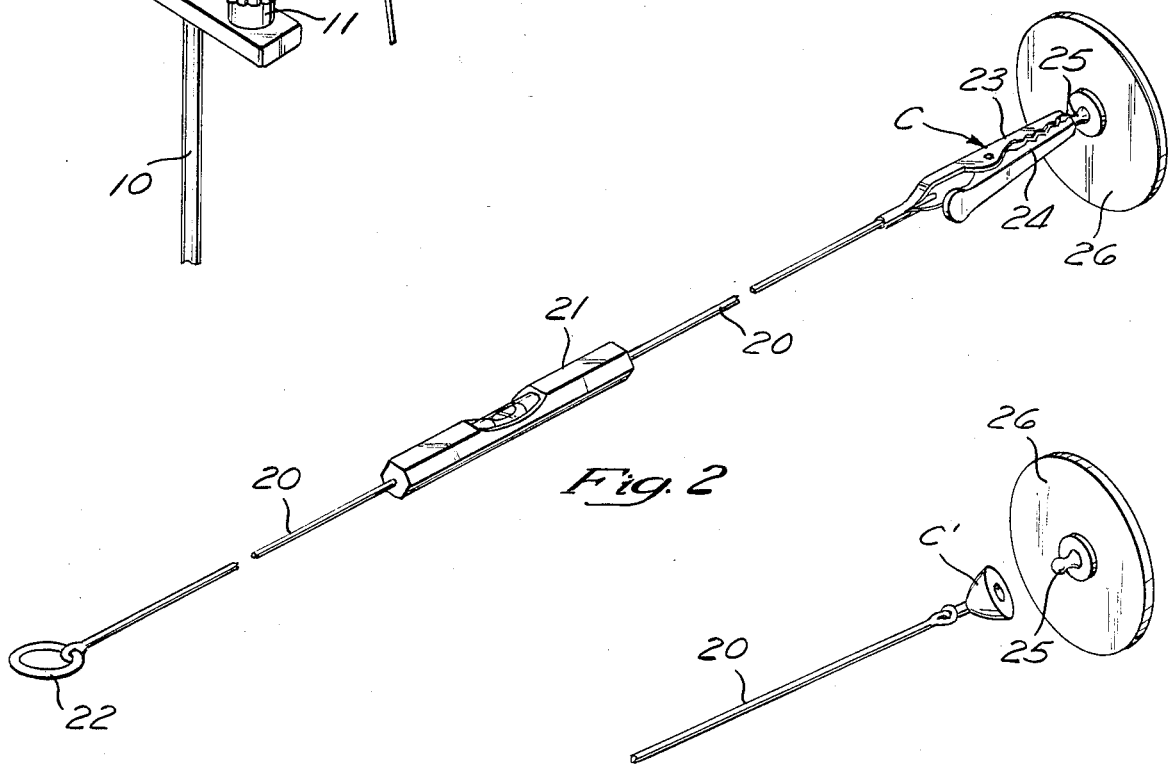
FIG. 2 is a perspective view of the present leveling device having an "alligator" spring clip on one end.

If desired, the adhesive patch 26 may be connected to the end of the line 20 in some other fashion, such as by a releasable connector different from the "alligator" clip C of FIG. 2 or the snap clip C' of FIG. 3.

I claim:

1. In combination with a vertically adjustable hemodynamic monitoring transducer assembly, a leveling device comprising:
   an elongated flexible line adapted to extend substantially taut between said transducer assembly and the chest of a patient whose heart is to be monitored;
   attachment means on one end of said line releasably attaching it to the transducer assembly;
   attachment means on an opposite end of said line for attaching it to the patient's chest at the level of the right atrium of the heart;
   and a small bubble level on said line between its ends to indicate whether it is horizontal.

2. A combination according to claim 1, wherein said attachment means on one end of the line is a loop.

3. A combination according to claim 2, wherein said attachment means on the opposite end of the line comprises a spring clip.

4. A combination according to claim 1, wherein said attachment means on the opposite end of the line comprises a spring clip.

5. In combination with a hemodynamic monitoring transducer assembly which is adjustable as a unit vertically on an IV stand, said transducer assembly including a strain gauge transducer and a stopcock having a hollow arm with an end cap that is removable to vent the transducer to the atmosphere, a leveling device comprising:
   an elongated flexible line carrying a small bubble level intermediate its ends;
   a loop on one end of said line inserted over said hollow arm of the stopcock in said transducer assembly;
   and means on an opposite end of said line for attaching the line to the patient's chest at the level of the right atrium of the heart.

6. A combination according to claim 5, wherein said means for attaching the opposite end of the line is a spring clip which is attachable to a post on an adhesive patch on the patient's chest.

* * * * *